United States Patent
Rechner

(10) Patent No.: US 9,052,258 B2
(45) Date of Patent: Jun. 9, 2015

(54) METHOD FOR STANDARDIZING MEASURED RESULTS IN A SYSTEM FOR MEASURING THROMBOCYTE FUNCTION

(75) Inventor: Andreas Rechner, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 260 days.

(21) Appl. No.: 13/541,846

(22) Filed: Jul. 5, 2012

(65) Prior Publication Data
US 2013/0008236 A1 Jan. 10, 2013

(30) Foreign Application Priority Data
Jul. 7, 2011 (EP) ..................................... 11172972

(51) Int. Cl.
G01N 33/86 (2006.01)
G01N 33/487 (2006.01)
G01N 11/04 (2006.01)
G01N 33/49 (2006.01)

(52) U.S. Cl.
CPC ............ *G01N 11/04* (2013.01); *G01N 33/4905* (2013.01)

(58) Field of Classification Search
CPC .... G01N 11/04; G01N 33/4905; G01N 33/86
USPC .................... 73/54.07, 53.01; 435/13; 436/69
See application file for complete search history.

(56) References Cited

U.S. PATENT DOCUMENTS

| | | | |
|---|---|---|---|
| 5,888,826 A | * | 3/1999 | Ostgaard et al. ................. 436/69 |
| 2007/0254324 A1 | | 11/2007 | Rechner |
| 2007/0254325 A1 | | 11/2007 | Rechner |

FOREIGN PATENT DOCUMENTS

| | | |
|---|---|---|
| EP | 1850134 A1 | 10/2007 |
| EP | 1850135 A1 | 10/2007 |
| WO | 9734698 A1 | 9/1997 |

OTHER PUBLICATIONS

European Search Report of European Patent Application No. EP 11 17 2972 issued on Nov. 23, 2011.
Rechner, A.R., "Platelet Function Testing in Clinical Diagnostics", Hämostaseologie Feb. 2011, 31: 79-87, Prepublished online on Dec. 9, 2010.
Böck et al., "Standardization of the PFA-100 Platelet Function Test in 105 mmol/l Buffered Citrate: Effect of Gender, Smoking, and Oral Contraceptives", 1999, British Journal of Haematology, 1999:106, 898-904.
Haubelt et al., "Variables Influencing Platelet Function Analyzer-100 Closure Times in Healthy Individuals", 2005, British Journal of Haematology, 130: 759-767.

* cited by examiner

*Primary Examiner* — Hezron E Williams
*Assistant Examiner* — David Z Huang
(74) *Attorney, Agent, or Firm* — King & Spalding L.L.P.

(57) ABSTRACT

The invention is in the field of coagulation diagnostics and relates to in vitro methods for determining thrombocyte function using measuring cells, particularly measuring cells of the PFA system. The methods make it possible to obtain standardized measured results which are comparable, irrespective of the type of measuring cell used.

6 Claims, 5 Drawing Sheets

METHOD FOR STANDARDIZING MEASURED RESULTS IN A SYSTEM FOR MEASURING THROMBOCYTE FUNCTION

PRIORITY STATEMENT

The present application hereby claims priority under 35 U.S.C. §119 of European Patent Application Number 11172972.9 filed Jul. 7, 2011, the entire contents of which are hereby incorporated herein by reference.

FIELD OF INVENTION

The invention is in the field of coagulation diagnostics and relates to in vitro methods for determining thrombocyte function using measuring cells. The methods make it possible to obtain measured results which are comparable, irrespective of the type of measuring cell used.

BACKGROUND OF INVENTION

Physiological processes which, firstly, ensure the fluidity of the blood in the vascular system and, secondly, make sure extravascular blood loss is avoided through the formation of blood clots come under the term hemostasis. The regulation of hemostasis involves a multiplicity of protein factors and also cellular components, for example thrombocytes (platelets). In the event of vascular injury, there is initially attachment of thrombocytes to the subendothelial collagen. This adhesion is mediated by adhesive proteins, such as von Willebrand factor (VWF). During the adhesion process, the thrombocytes are activated and release mediators from their granules, inducing the aggregation of further thrombocytes and intensification of activation. This achieves primary vascular wall occlusion (primary hemostasis), which needs further reactions of the plasmatic coagulation system (secondary hemostasis) to stabilize it. Dysregulation of these processes may lead to thrombophilia or bleeding diathesis and, depending on the severity, life-threatening sequelae.

In coagulation diagnostics, various methods and systems are known which make it possible to determine whether the blood of a patient can coagulate properly or whether a coagulation defect is present. In the event of a coagulation defect, it is often necessary to obtain more precise information about the cause of the defect present in order to be able to select optimal therapeutic measures. An important subfunction of the coagulation system which can be tested specifically is primary hemostasis, which depends substantially on the functional efficiency of thrombocytes.

One known method for testing thrombocyte function is that of bleeding time determination. This is an in vivo global test which captures primary hemostasis. The bleeding time is determined by causing the patient a small cutting or stabbing injury and measuring the time for bleeding to stop. This is a rough, difficult-to-standardize test which is used especially in emergency situations to obtain a snapshot of primary hemostasis. The intake of thrombocyte aggregation inhibitors leads to prolongation of bleeding time. A disadvantage of bleeding time determination is that even if bleeding time is normal, a thrombocyte function defect cannot be ruled out.

In vitro methods permit substantially more sensitive detection of thrombocyte function defects. Typically, in these methods, aggregation of thrombocytes is induced in a whole blood sample or in a sample of platelet-rich plasma (PRP) by addition of an activator and the aggregation reaction is measured. The most commonly used activators to induce thrombocyte aggregation are: ADP (adenosine 5'-diphosphate), collagen, epinephrine (adrenaline), ristocetin and various combinations thereof and thrombin, TRAP (thrombin receptor activating protein), U-46619, heparin (especially in the case of heparin-induced thrombocytopenia) or serotonin.

One known system for determining thrombocyte function in vitro is what is known as the Platelet Function Analyzer system, or PFA system for short (PFA-100®, PFA-200, Siemens Healthcare Diagnostics Products GmbH, Marburg, Germany). Using the PFA system, primary hemostasis is measured in whole blood samples under flow conditions and hence in the presence of high shear forces.

To simulate the flow conditions and the shear forces which prevail minor arterial blood vessels, a negative pressure of about −40 mbar is generated in a PFA measuring cell inserted into a PFA analysis device, and the citrated whole blood, which is located in a sample reservoir, flows through a capillary which has a diameter of about 200 μm. The capillary opens into a measuring chamber which is closed off by a partition element, for example a membrane, which contains a central capillary aperture through which the blood flows owing to the negative pressure. In most cases, the membrane, at least in the region around the aperture, contains one or more activators which induce thrombocyte aggregation, and so the blood which flows past comes into contact with the aggregation-inducing substances in the region of the aperture. The induced adhesion and aggregation of the thrombocytes results, in the region of the aperture, in the formation of a platelet plug (thrombus) which closes the membrane aperture and stops the blood flow. In this system, the time to closure of the membrane aperture is measured. This "closure time" correlates with the functional efficiency of the thrombocytes. A measuring cell for use in a method for determining thrombocyte function on the basis of closure time is, for example, described in the patent document WO 97/34698. To date, the method for determining closure time uses measuring cells which have a membrane coated with collagen (Col) and additionally either ADP or epinephrine (Epi). Other measuring cells which are especially suitable for determining antithrombotics from the group of the P2Y(12) antagonists, for example clopidogrel, have a membrane which contains ADP and prostaglandin E1 (INNOVANCE® PFA P2Y, EP-A1-1850134).

One known method for determining thrombocyte function in a sample using a PFA system comprises the following steps:
  a) using a measuring cell, wherein the measuring cell comprises the following elements:
  a retention chamber for retaining the sample,
  b) a capillary through which the sample is conducted from the retention chamber into a measuring chamber,
  c) a measuring chamber which is divided by a partition element into two compartments, wherein the first compartment accommodates the sample from the capillary,
  d) a partition element which divides the measuring chamber into two compartments and which has an aperture through which the sample can flow from the first compartment into the second compartment;
  e) filling the retention chamber of the measuring cell with the sample;
  f) placing the measuring cell in a device for automatic determination of thrombocyte function, wherein the device comprises the following elements:
  means for applying negative pressure in the measuring chamber of the measuring cell,
  g) means for determining the total volume which, as a result of the application of negative pressure, is drawn from the measuring cell when negative pressure is applied in the measuring chamber of the measuring cell;

h) applying negative pressure in the measuring chamber of the measuring cell and conducting the sample through the capillary and through the aperture in the partition element.

The total volume which, as a result of the application of negative pressure, is drawn from the measuring cell is continuously determined. The flow rate (μL/min) is determined from the volume which is drawn from the measuring cell per unit time.

The flow rate typically decreases over time, since the platelet plug gradually constricts the aperture and thus makes it difficult for the sample liquid to pass through.

The test result provided is the closure time in seconds. Closure time is defined as the time at which the flow rate was less than 10% of the initial flow rate for a period of three seconds. The initial flow rate is the flow rate at the start of the measurement when no platelet plug has yet formed at the aperture, but the dead volume has already been drawn from the system.

If the closure time of a patient's sample deviates from the reference range, this indicates a defect in thrombocyte function. Extended closure times indicate that there is thrombocyte dysfunction in terms of reduced aggregation ability. Shortened closure times indicate that there is thrombocyte dysfunction in terms of increased aggregation ability.

The closure time of a sample from a healthy donor with normal thrombocyte function depends on many factors.

Closure time is primarily affected by the type of measuring cell used. As explained above, measuring cells are used which contain different combinations of thrombocyte activators or thrombocyte inhibitors. When using a measuring cell containing collagen and epinephrine (Col/Epi), the closure time of a normal sample is between 84-160 seconds. When using a measuring cell containing collagen and ADP (Col/ADP), the closure time of a normal sample is between 68-121 seconds. When using a measuring cell containing ADP and prostaglandin E1 (ADP/PGE1), the closure time of a normal sample is below 106 seconds. The large variations in the reference ranges have the disadvantage that a closure time as such is not meaningful, but can only ever be interpreted in connection with the type of measuring cell used. A closure time of, for example, 130 seconds is a normal result for Col/Epi measuring cells, but an abnormal result for Col/ADP or ADP/PGE1 measuring cells in that it implies bleeding diathesis.

A further factor influencing closure time is the measuring cell architecture. Different diameters of the aperture or the capillary affect thrombus formation and hence the rate at which the aperture is closed.

SUMMARY OF INVENTION

It is therefore desirable to improve the above-described known method for determining thrombocyte function such that the measurement of thrombocyte function in a PFA system can be harmonized and standardized for all types of measuring cell used, and so the measured results are directly comparable, irrespective of which type of measuring cell is used.

This object is achieved by determining the sample volume passing within a defined time interval through the aperture in the partition element and then comparing the determined sample volume value with a reference sample volume value for normal thrombocyte function.

BRIEF DESCRIPTION OF THE DRAWINGS

A more complete appreciation of the present invention and many of the attendant advantages thereof will be readily understood by reference to the following detailed description when taken in conjunction with the accompanying drawings, in which.

DETAILED DESCRIPTION OF INVENTION

The sample volume passing within a defined time interval through the aperture in the partition element is preferably determined by measuring the total volume which, as a result of the application of negative pressure, is drawn from the measuring cell and determining the difference between the measured total volume and the dead volume of the measuring cell used.

Figure 5:
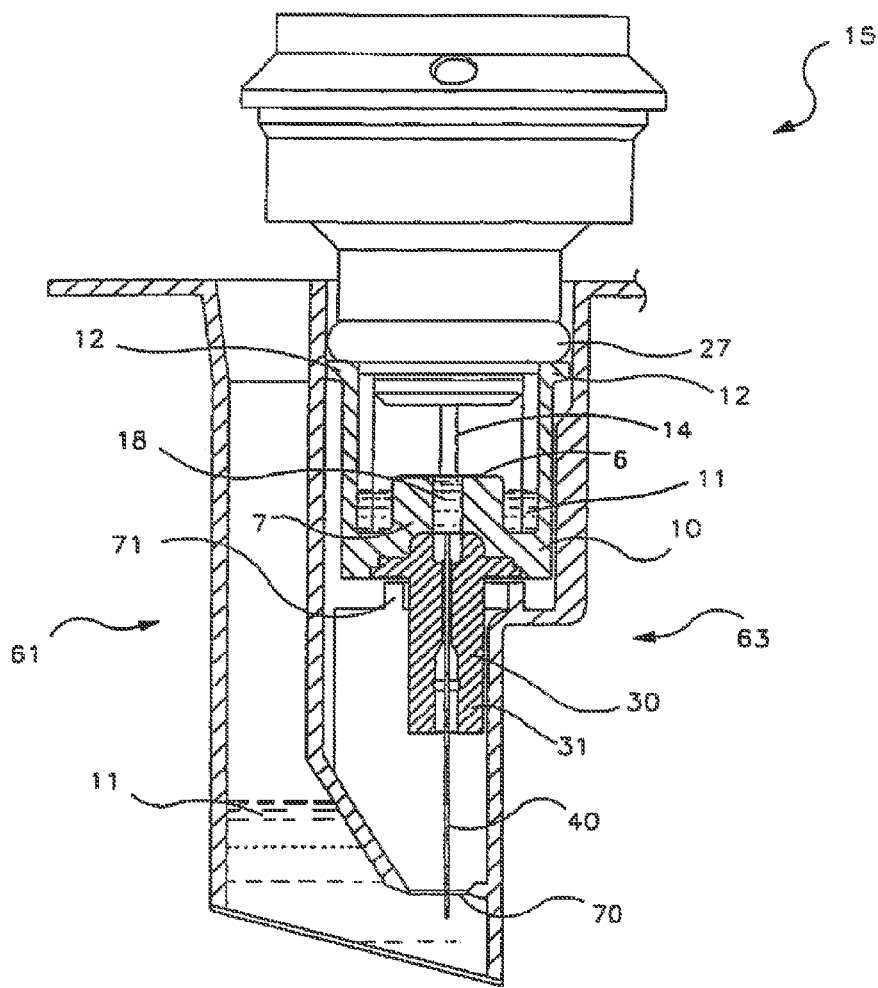
FIG. 5 is an example of a test cartridge that may be used in accordance with embodiments.

FIG. 5 shows by way of example how a device for the determination of platelet function according to the invention can be constructed. Shown is a test cartridge in accordance with WO 97/34698 in longitudinal section that is placed in a suitable apparatus for implementing the method according to the invention and into which extends a vacuum apparatus (15) that is responsible for the generation of the partial vacuum The vacuum apparatus (15) has a ring gasket (27) which is located as a seal on the circumferential edge (12) of the sample container (10). The test cartridge has a housing that forms a reservoir (61) and a test chamber (63) The test chamber (63) is constructed to accept a sample container (10) the cavity of which can also be referred to as measurement chamber. The sample container (10) supports a partition member (6) treated with reagents and with a central opening (aperture) and a capillary attachment (30, 31) that connects the capillary (40) with the sample container (10), Reservoir (61) and test chamber (63) are separated by a penetrable element (70). The figure shows a phase of the test cycle after the vacuum apparatus (15) is in contact with sample container (10) and has moved downwards so that the base of the sample container (10) is in contact with the support (71) and the capillary (40) has penetrated the penetrable element (70) and penetrated into the sample (11). The apparatus produces a partial vacuum in the sample container (10) by means of which the sample (11) is pulled through the capillary (40) into the first compartment (18) of the measurement chamber and then through the opening in the partition member (6).

Measurement of the total volume which, as a result of the application of negative pressure, is drawn from the measuring cell when negative pressure is applied in the measuring chamber of the measuring cell can, as will be known, be determined by measuring the volume which the means for applying negative pressure in the measuring chamber of the measuring cell draws from the measuring cell. The means for applying negative pressure preferably consists of a cylinder having a plunger, the plunger being movable in the axial direction of the cylinder via a stepper motor and a plunger rod. Negative pressure is generated in the measuring cell by moving the plunger. In the measuring chamber of the measuring cell, or in the space which is created by connecting the measuring cell to the cylinder and in which the negative pressure is built up, a pressure sensor measures the prevailing pressure. A control unit compares the measured pressure with a preset target pressure. The pressure increases when blood flows into the capillary. To keep the pressure constant, for example at −40 mbar, the control unit controls the stepper motor, which moves the plunger accordingly in an axial manner. The path covered by the plunger in the cylinder of known diameter can be used to calculate the total volume which is drawn from the measuring cell.

The total volume which is drawn from the measuring cell is composed of the dead volume of the measuring cell and the volume of the sample which has actually passed through the aperture in the partition element (sample volume). The difference between the measured total volume and the known measuring cell-specific dead volume gives the sample volume which passes through the aperture in the partition element within a defined time interval or until closure of the aperture.

The dead volume of a measuring cell corresponds to the volume which, when negative pressure is applied in the measuring chamber of the measuring cell, passes through the aperture in the partition element before sample liquid passes through the partition element for the first time. The dead volume of a measuring cell typically consists of air which is present particularly in the capillary of the measuring cell and in the measuring chamber compartment which is situated in front of the partition element and accommodates the sample from the capillary.

The dead volume depends on the measuring cell architecture. The dead volume of a specific type of measuring cell can be calculated, or it is determined experimentally in advance. For experimental determination, preferably the dead volume of multiple measuring cells of the same type is determined and the median of the measured dead volumes is applied as the dead volume for measuring cells of this type.

Alternatively, the sample volume passing through the aperture in the partition element within a defined time interval can be determined by electronically or optically determining the fill level of the sample volume in the second compartment of the measuring chamber.

The determined sample volume value is then compared with a reference sample volume value for normal thrombocyte function.

The reference sample volume value for normal thrombocyte function depends on the type of measuring cell used, and the value is determined experimentally in advance. For experimental determination, the sample volume of a sufficiently large number of samples from apparently healthy blood donors (normal samples) which passes through the aperture in the partition element within a defined time interval or until closure of the aperture is determined in measuring cells of the same type, and the median of the measured sample volumes is applied as the reference sample volume value for measuring cells of this type.

Preferably, the determined sample volume is expressed in relation to a reference sample volume value for normal thrombocyte function. Particularly preferably, the reference sample volume value for normal thrombocyte function is 100%. A test result thus determined is a measure of the thrombocyte function compared to the norm (% of the norm). It can also be referred to as primary hemostasis capacity 1 (PHC 1).

An example of a formula for the calculation is as follows ("formula (1)"):

$$PHC(1)\% = \frac{(TV_{median} - DV_{median}) \times 100}{(TV - DV_{median})}$$

where
$TV_{median}$=median total volume for normal thrombocyte function,
$DV_{median}$=median dead volume for type of measuring cell used,
TV=total volume of sample to be analyzed.

The object of the invention is also achieved by determining the sample volume passing through the aperture in the partition element within a defined time interval, determining the initial flow rate, then calculating the difference between five times the initial flow rate and the sample volume and then comparing the difference with a reference difference value for normal thrombocyte function.

The sample volume is determined as already described above.

The initial flow rate is the maximum flow rate of the sample liquid at the start of the measurement. The initial flow rate is preferably determined by continuously determining the flow rate, i.e., the volume which is drawn from the measuring cell per unit time, from the start of the measurement, i.e., from the time at which negative pressure is applied in the measuring chamber of the measuring cell. At the very start of the measurement, there are certain fluctuations in the flow rate owing, inter alia, to the initially aspirated dead volume, until eventually a continuously decreasing flow rate becomes established. The initial flow rate is defined as the flow rate which was measured before the flow rate eventually decreases continuously for at least 10 seconds.

The difference between five times the determined initial flow rate and the determined sample volume is calculated, and the difference is then compared with a reference difference value for normal thrombocyte function.

The reference difference value is determined individually for each sample measurement by calculating the difference between five times the measured sample-specific initial flow rate and the previously determined reference sample volume value for normal thrombocyte function. The reference sample volume value for normal thrombocyte function is determined as already described above.

Preferably, the difference determined between five times the determined initial flow rate and the determined sample volume is expressed in relation to a reference difference value for normal thrombocyte function. Particularly preferably, the reference difference value for normal thrombocyte function is 100%. A test result thus determined is a measure of the thrombocyte function compared to the norm (% of the norm). It can also be referred to as primary hemostasis capacity 2 (PHC 2).

An example of a formula for the calculation is as follows ("formula (2)"):

$$PHC(2)\% = \frac{(5 \min \times IF - (TV_{median} - DV_{median})) \times 100}{5 \min \times IF - (TV - DV_{median})}$$

where

IF=initial flow rate of sample to be analyzed,
$TV_{median}$=median total volume for normal thrombocyte function,
$DV_{median}$=median dead volume for type of measuring cell used,
TV=total volume of sample to be analyzed.

The advantage of the present invention is that, irrespective of the type of measuring cell used, i.e., irrespective of the type of thrombocyte-activating or -inhibiting substances used and irrespective of the measuring cell architecture, samples with lowered thrombocyte function (risk of bleeding) always have test results of less than 100% and samples with increased thrombocyte function (risk of thrombosis) always have test results of greater than 100%. The normal ranges of various measuring cell types scarcely differ owing to this standardization.

DESCRIPTION OF FIGURES

Figure 1:
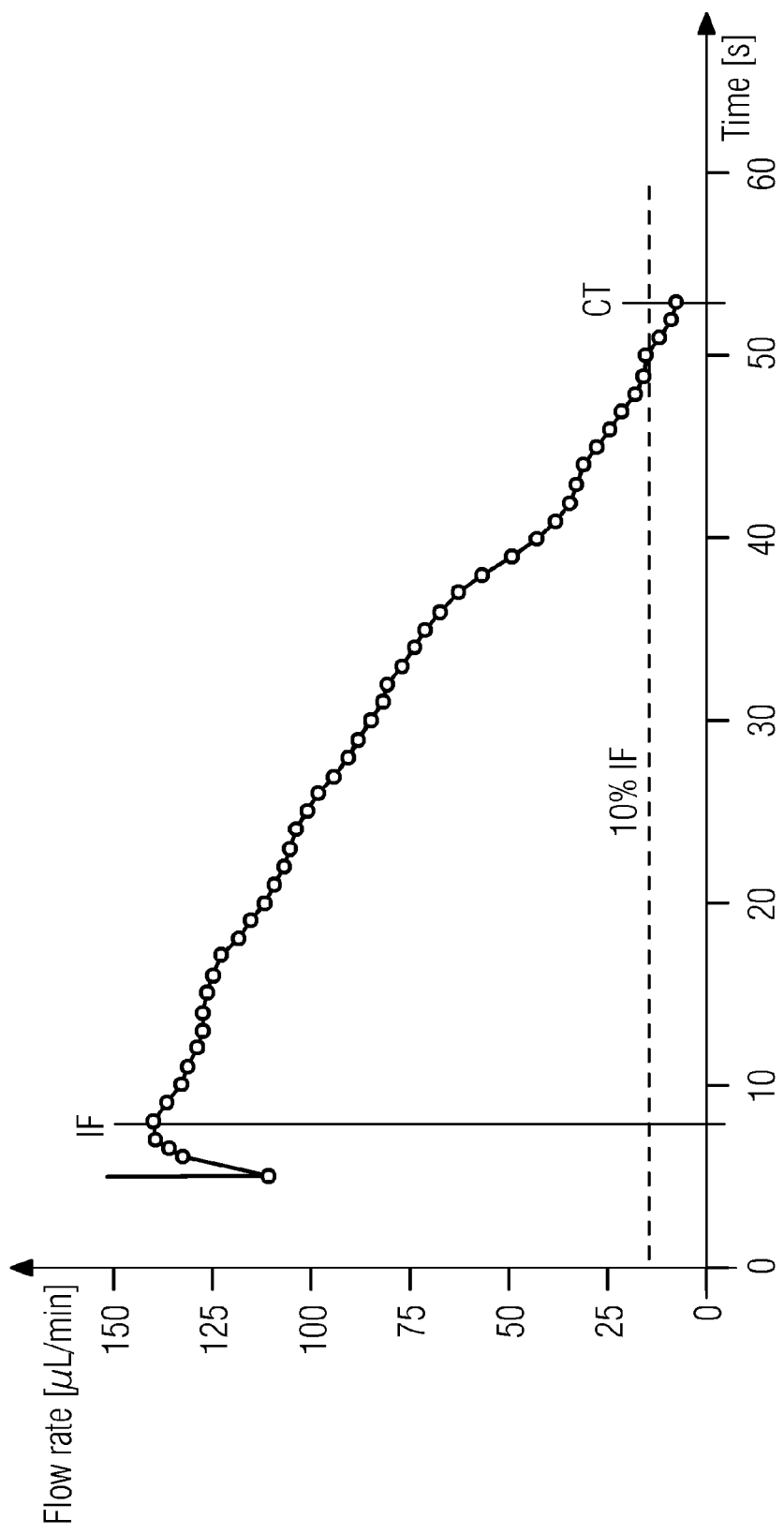
FIG. 1 shows a typical flow curve of a whole blood sample from a healthy donor with normal thrombocyte activity in an INNOVANCE PFA P2Y measuring cell.

FIG. 1 shows a typical flow curve of a whole blood sample from a healthy donor with normal thrombocyte activity in an INNOVANCE PFA P2Y measuring cell. After initial fluctuations in the flow rate at the start of the measurement, a continuously decreasing flow rate emerges. The flow rate measured at the start of the continuous decrease is the initial flow rate (IF). The closure time (CT) is defined as the time at which the flow rate was less than 10% of the initial flow rate for a period of three seconds.

Figure 2:
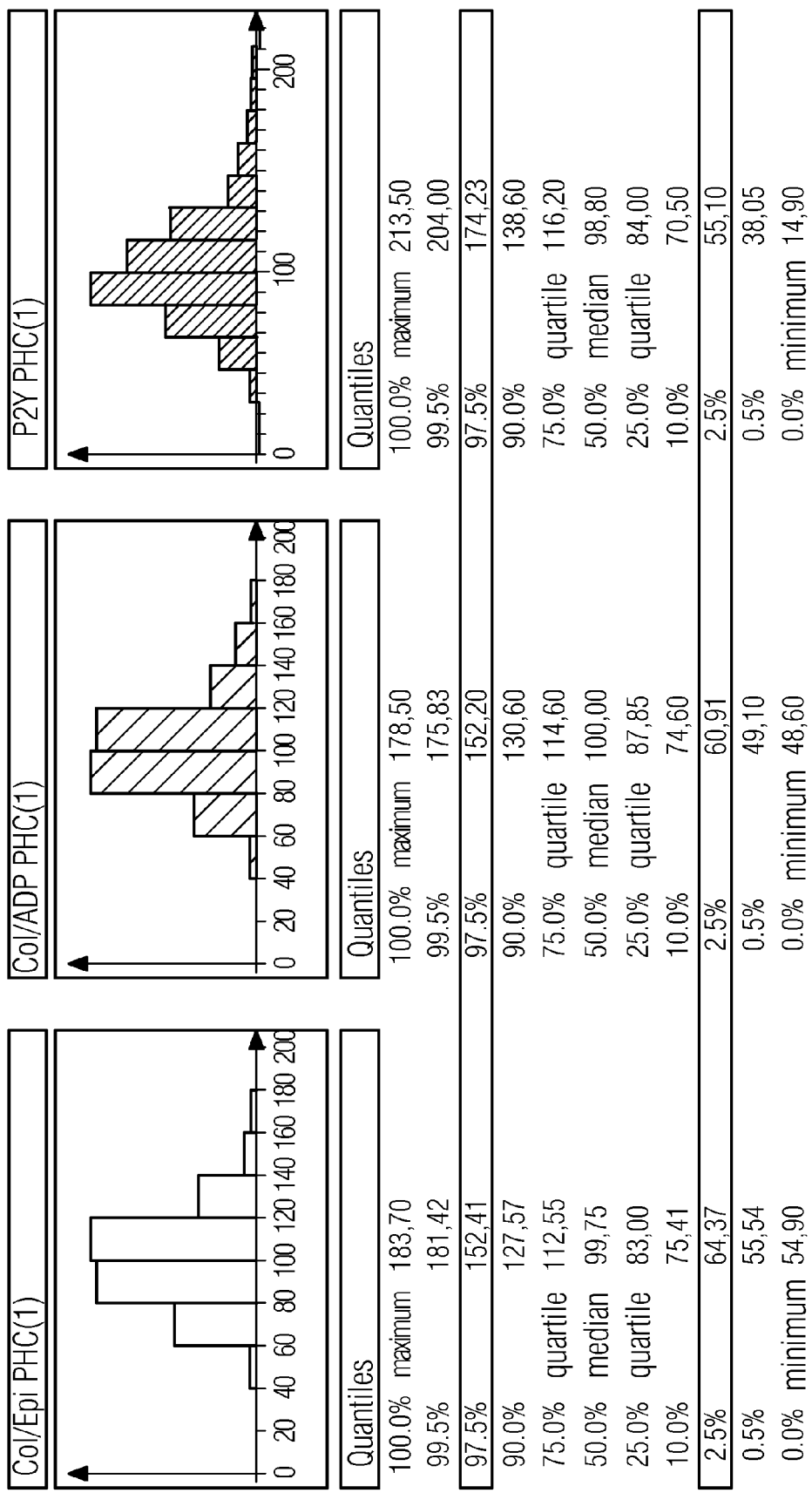
FIG. 2 shows the distribution and percentiles of the PHC(1) values from determinations of the thrombocyte activity in whole blood samples from healthy donors (N=138 healthy blood donors) using Col/Epi, Col/ADP and INNOVANCE PFA P2Y (P2Y) measuring cells.

FIG. 2 shows the distribution and percentiles of the PHC(1) values from determinations of the thrombocyte activity in whole blood samples from healthy donors (N=138 healthy blood donors) using Col/Epi, Col/ADP and INNOVANCE PFA P2Y (P2Y) measuring cells. It is apparent that the upper and lower limits of the 95% central intervals of PHC(1) of all three types of measuring cell are close to each other.

Figure 3:
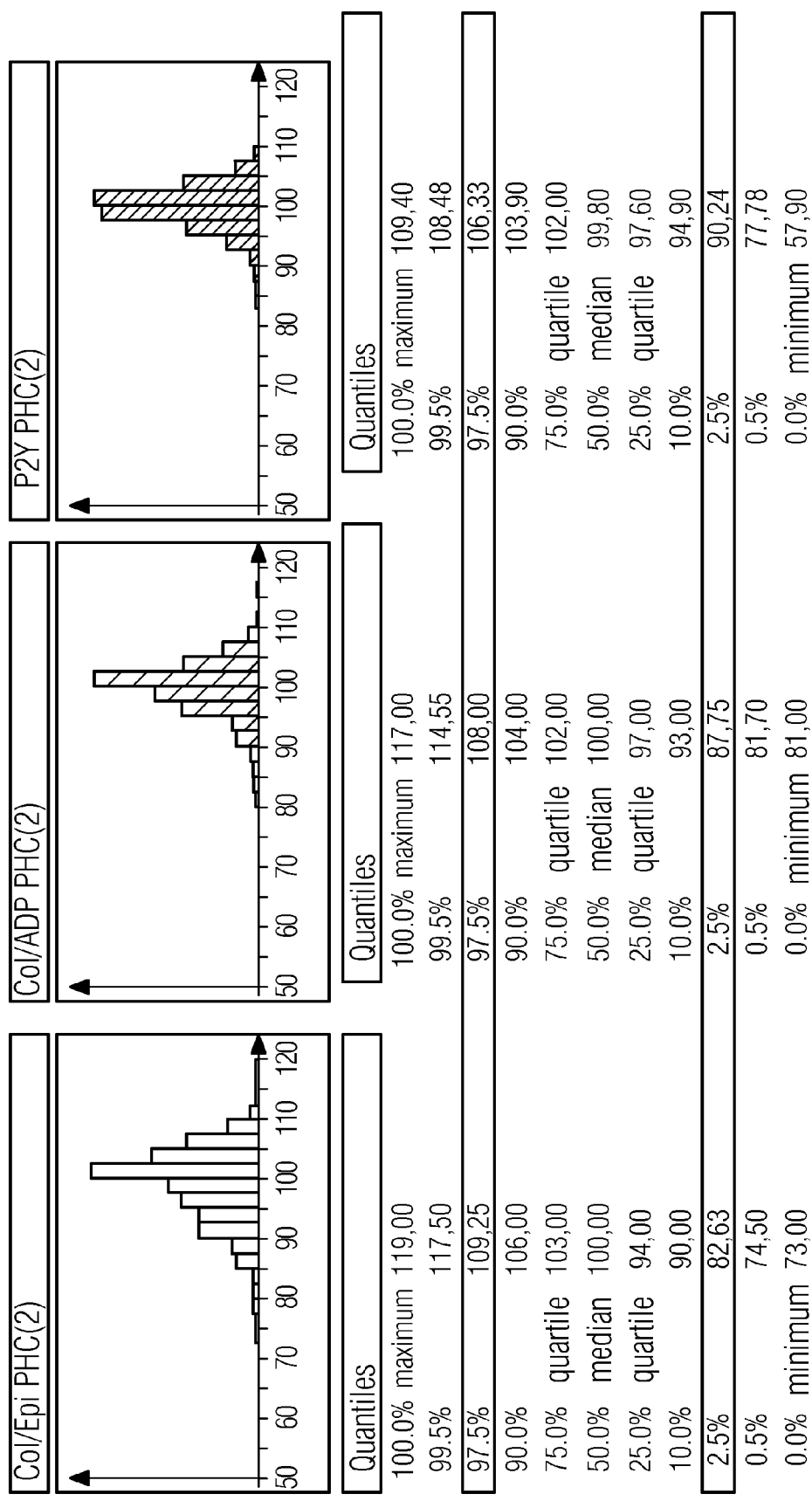
FIG. 3 shows the distribution and percentiles of the PHC(2) values from determinations of the thrombocyte activity in whole blood samples from healthy donors (N=138 healthy blood donors) using Col/Epi, Col/ADP and INNOVANCE PFA P2Y (P2Y) measuring cells.

FIG. 3 shows the distribution and percentiles of the PHC(2) values from determinations of the thrombocyte activity in whole blood samples from healthy donors (N=138 healthy blood donors) using Col/Epi, Col/ADP and INNOVANCE PFA P2Y (P2Y) measuring cells. It is again apparent that the upper and lower limits of the 95% central intervals of PHC(2) of all three types measuring cell are close to each other.

Figure 4:
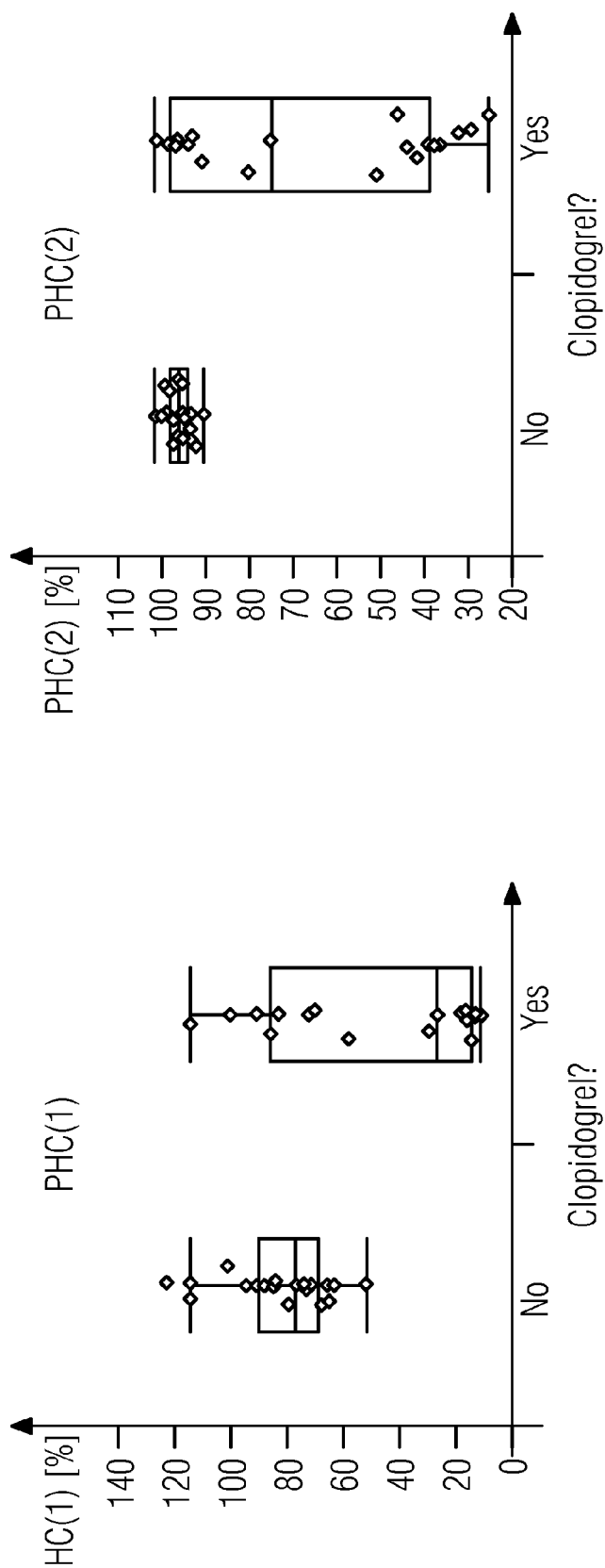
FIG. 4 shows the distribution of the PHC(1) and PHC(2) values from determinations of the thrombocyte activity in whole blood samples from cardiology patients before (N=23) and after (N=23) clopidogrel intake using INNOVANCE PFA P2Y measuring cells.

FIG. 4 shows the distribution of the PHC(1) and PHC(2) values from determinations of the thrombocyte activity in whole blood samples from cardiology patients before (N=23) and after (N=23) clopidogrel intake using INNOVANCE PFA P2Y measuring cells. It is apparent that both PHC(1) and PHC(2) provide differentiable results even in the case of greatly reduced thrombocyte function.

EXAMPLES

The following examples illustrate the invention and are not to be understood as limiting it.

Example 1

Determination of Thrombocyte Function as % of the Norm by Means of PHC(1) and PHC(2) in Samples from Healthy Donors Blood samples from 138 healthy blood donors in 3.2% and 3.8% buffered sodium citrate were measured in duplicate using three different types of PFA measuring cell in a PFA device (PFA-100, Siemens Healthcare Diagnostics Products GmbH). Measuring cells having a membrane with a collagen (Col) and ADP coating (Col/ADP), or a collagen (Col) and epinephrine (Epi) coating (Col/Epi), or an ADP and prostaglandin E1 coating (INNOVANCE® PFA P2Y; P2Y for short) were used. The total volume, the dead volume (air volume which is drawn from the measuring cell during the first four seconds of the measurement) and the initial flow rate were determined from the raw data determined by the device. Total volume and dead volume of all measurements (four measurements with P2Y measuring cells and two measurements with Col/Epi and Col/ADP measuring cells per donor) were then used to calculate median total volume for normal thrombocyte function ($TV_{median}$) i.e., the reference sample volume value for normal thrombocyte function, and median dead volume for the type of measuring cell used ($DV_{median}$) The median values are shown in table 1.

TABLE 1

| Measuring cell type | $TV_{median}$ [μL] | $DV_{median}$ [μL] |
|---|---|---|
| Col/ADP | 300 | 159 |
| Col/Epi | 350 | 159 |
| P2Y | 223 | 144 |

These median values were used in the above-mentioned formulae (1) and (2) as constants for the calculation of the thrombocyte function, as % of the norm, of each sample.

The distribution of the normalized PHC(1) values is shown in FIG. 2. The distribution of the PHC(2) values is shown in FIG. 3.

It is apparent that the upper and lower limits of the 95% central intervals of PHC(1) and PHC(2) of the three types of measuring cell are fairly close to each other. The small differences can be attributed to the measuring cell characteristics, for example the potency and concentration of the thrombocyte agonists used.

Thrombocyte function results determined using the method according to the invention are directly comparable, irrespective of which type of measuring cell is used.

Example 2

Determination of Thrombocyte Function as % of the Norm by Means of PHC(1) and PHC(2) in Samples from Anticoagulated Patients The effect of taking of clopidogrel, an inhibitor of thrombocyte function, on the PHC(1) and PHC(2) values of INNOVANCE PFA P2Y measurements was investigated with the help of cardiology patients. To this end, blood was collected in 3.2% buffered sodium citrate from each patient before and at least 4 hours after taking of clopidogrel (300 mg), and thrombocyte activity was measured using INNOVANCE PFA P2Y measuring cells. For the calculation of the thrombocyte function, as % of the norm, of each sample, the median values as shown in table 1 were used. FIG. 4 displays the PHC(1) and PHC(2) values before and after clopidogrel intake.

It is apparent that both PHC(1) and PHC(2) provide differentiable results even when there is greatly reduced thrombocyte function, and this is not the case for closure time, which is typically used, since in this event all results are reported as >300 s.

The invention claimed is:
1. A method for determining thrombocyte function in a sample, wherein the method comprises the following steps:
 a) using a measuring cell, wherein the measuring cell comprises the following elements:
  i) a retention chamber for retaining the sample, ii) a capillary through which the sample is conducted from the retention chamber into a measuring chamber, iii) a measuring chamber which is divided by a partition element into two compartments, wherein the first compartment accommodates the sample from the capillary, iv) a partition element which divides the measuring chamber into two compartments and which has an aperture through which the sample can flow from the first compartment into the second compartment;

b) filling the retention chamber of the measuring cell with the sample;

c) placing the measuring cell in a device for automatic determination of thrombocyte function, wherein the device comprises the following elements:

i) means for applying negative pressure in the measuring chamber of the measuring cell, ii) means for determining the total volume which, as a result of the application of negative pressure, is drawn from the measuring cell when negative pressure is applied in the measuring chamber of the measuring cell;

d) applying negative pressure in the measuring chamber of the measuring cell and conducting the sample through the capillary and through the aperture in the partition element; and wherein the method further comprises the following steps:

e) determining the sample volume passing within a defined time interval through the aperture in the partition element, and f) comparing the determined sample volume with a reference sample volume value for normal thrombocyte function; or g) determining the sample volume passing within a defined time interval through the aperture in the partition element, and h) determining the initial flow rate, and i) calculating the difference between five times the initial flow rate and the sample volume and comparing the difference with a reference difference value for normal thrombocyte function.

2. The method as claimed in claim 1, wherein, in step e) or in step g), the sample volume passing through the aperture in the partition element within a defined time interval is determined by measuring the total volume which, as a result of the application of negative pressure, is drawn from the measuring cell and determining the difference between the measured total volume and the dead volume of the measuring cell used.

3. The method as claimed in claim 1, wherein, in step f), the determined sample volume is expressed in relation to a reference sample volume value for normal thrombocyte function.

4. The method as claimed in claim 3, wherein the reference sample volume value for normal thrombocyte function is 100%.

5. The method as claimed in claim 1, wherein, in step i), the calculated difference is expressed in relation to a reference difference value for normal thrombocyte function.

6. The method as claimed in claim 5, wherein the reference difference value for normal thrombocyte function is 100%.

* * * * *